United States Patent [19]
Perez

[11] Patent Number: 5,528,151
[45] Date of Patent: Jun. 18, 1996

[54] THERMAL FATIGUE TESTING USING PLURAL TEST TRIPS WITH GRADUATED SIZING AND RECESSED ANCHORING

[75] Inventor: Frank A. Perez, Pasadena, Calif. 4

[73] Assignee: Hughes Aircraft Company, Los Angeles, Calif.

[21] Appl. No.: 973,499

[22] Filed: Nov. 9, 1992

[51] Int. Cl.⁶ ................................................ G01B 7/16
[52] U.S. Cl. ........................ 324/525; 324/555; 374/56; 374/187; 73/767; 73/774
[58] Field of Search ............................ 73/767, 774, 775, 73/781; 374/55, 56, 57, 45, 187; 324/537, 555, 525, 550

[56] References Cited

U.S. PATENT DOCUMENTS

| | | |
|---|---|---|
| 3,272,003 | 9/1966 | Harting ............................... 73/775 |
| 3,738,162 | 6/1973 | Dally et al. ......................... 73/775 |
| 3,786,679 | 1/1974 | Crites ................................. 73/767 |
| 3,828,606 | 8/1974 | Wolter ................................ 374/45 |
| 4,104,605 | 8/1978 | Boudreaux et al. ............... 338/2 |
| 4,590,804 | 5/1986 | Brull ................................... 73/762 |
| 4,793,189 | 12/1988 | Dell'Orto et al. ................. 73/775 |

Primary Examiner—Kenneth A. Wieder
Assistant Examiner—Christopher Tobin
Attorney, Agent, or Firm—Leonard A. Alkov; W. K. Denson-Low

[57] ABSTRACT

A plurality of fatigue life test strips (16, 18, 20, 22) has each of the strips anchored to a base (12) which is subject to thermal cycling and consequent dimensional change which causes fatigue. The base is, at best, semiconductive, and the strips are conductive. The conductivity of each of the strips is measured by test circuit (52) so that, when one fails due to fatiguing, the failure is signaled.

6 Claims, 2 Drawing Sheets

U.S. Patent   Jun. 18, 1996   Sheet 1 of 2   5,528,151
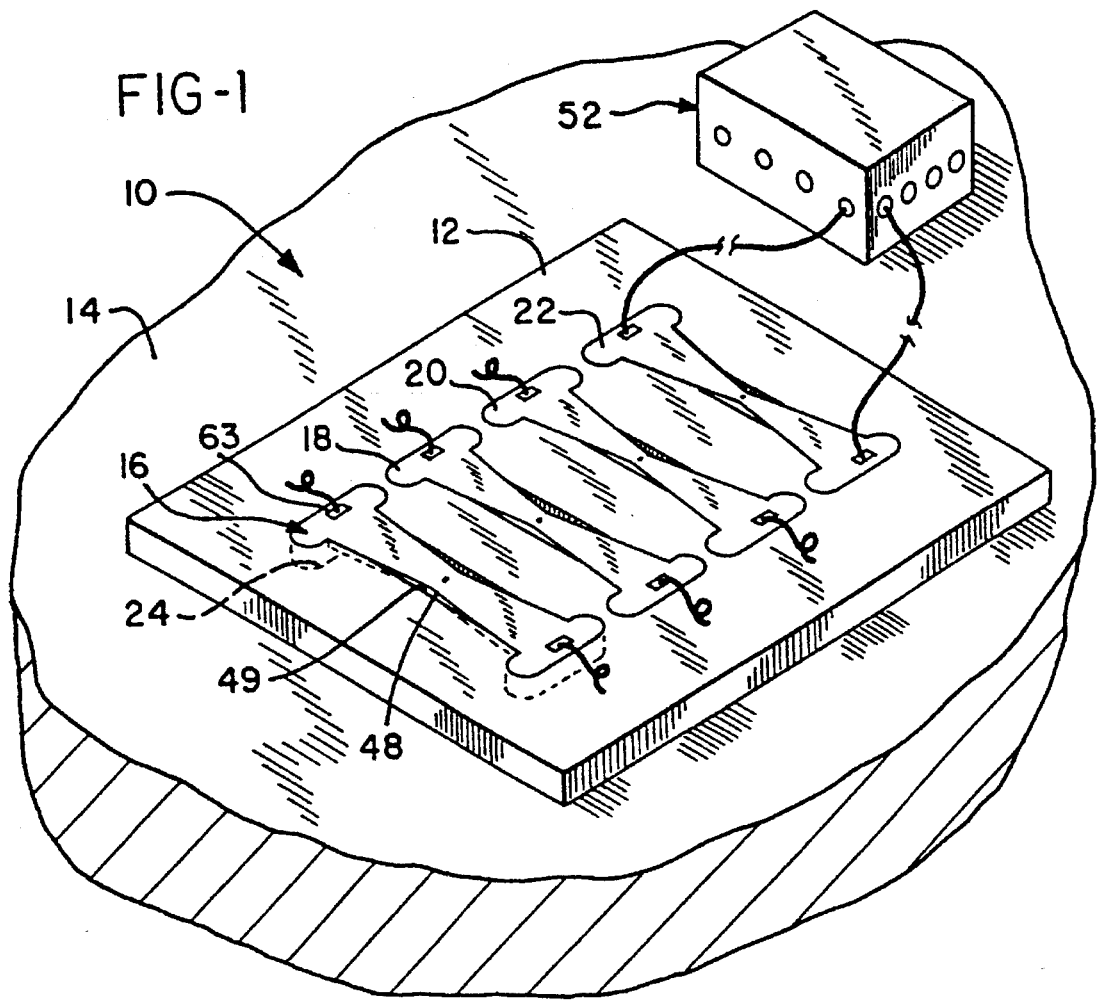
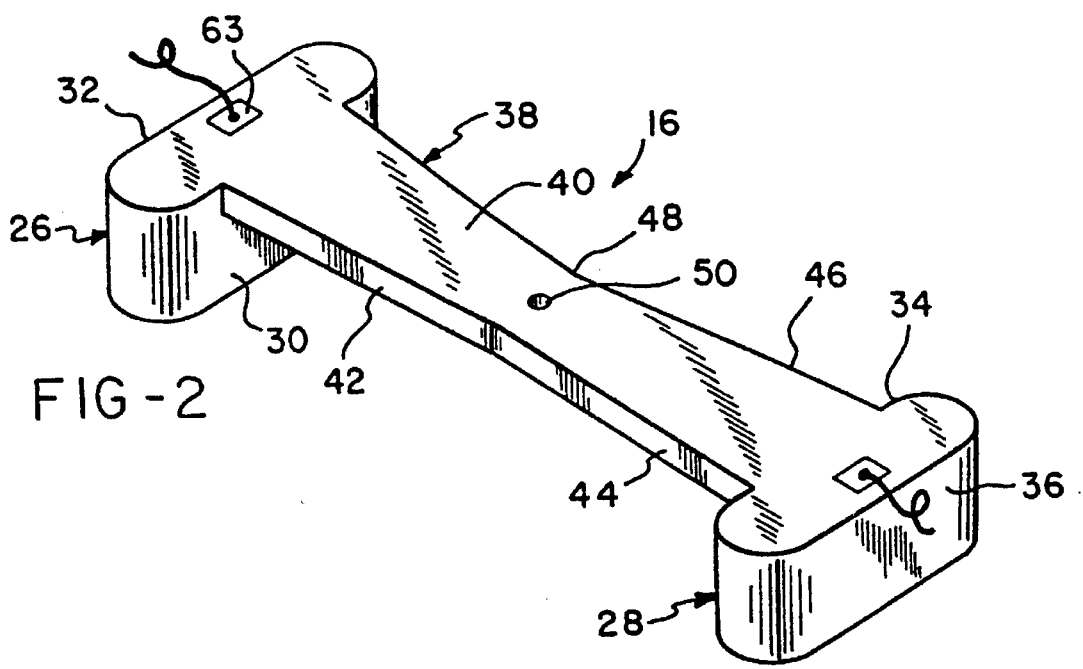

THERMAL FATIGUE TESTING USING PLURAL TEST TRIPS WITH GRADUATED SIZING AND RECESSED ANCHORING

FIELD OF THE INVENTION

This invention is directed to a method and apparatus wherein the fatigue failure of a structure of different materials due to thermal cycling can be predicted by the fatigue failure of test strips of a second material attached to a base of first material.

BACKGROUND OF THE INVENTION

Even when stressed below its ultimate strength, repeated stress on a mechanical part can cause failure due to fatigue. Fatigue life has been studied in many materials, and particularly those materials which are employed in the building of structures which are intended to have long life, but which are designed close to the ultimate strength limit. Such structures are subject to fatigue failure when repetitive stresses below the ultimate strength are encountered. Fatigue strength is principally a function of the materials, the manner in which the material has been treated, temperature, the amount of stress, and the number of cycles.

In the various fields of electronics, there is a wide variety of materials used in physical conjunction with each other. Semiconductor materials are connected by metal connectors and are mounted on non-conductive bases, such as ceramic or filled organic bases. Each of these structures has different thermal expansion properties and, as a result of thermal cycling, fatigue stresses are created and fatigue failure can take place. It is important in many electronic structures to be able to predict fatigue failure so that a part can be replaced before failure. When electronic assemblies are in operation, the remaining useful life is unknown, but many fail due to separation of different parts due to repeated thermal stress. A thermal fatigue testing method and apparatus therein will allow monitoring of leftover life.

SUMMARY OF THE INVENTION

In order to aid in the understanding of this invention, it can be stated in essentially summary form that it is directed to a fatigue testing method and apparatus wherein each of a plurality of fatigue life test strips is anchored in a base so that the test strips are subject to the same fatigue cycling as the parent structure, which may be on the same base. Electrical monitoring of the continuity of each test strip signals its failure by fatigue due to stress cycling to predict the remaining life in the associated structure.

It is thus a purpose and advantage of this invention to provide a thermal fatigue testing method and apparatus which is suitable for application to the structure which is subject to repeated stress which causes fatigue failure and to signal when fatigue failure is incipient.

It is another purpose and advantage of this invention to provide a fatigue testing method and apparatus wherein test strips are incorporated into an electronic device and are electrically tested for continuity so as to signal fatigue failure of the test strips.

It is another purpose and advantage of this invention to mount a fatigue test apparatus directly on an electronic device so as to signal incipient fatigue failure between dissimilar parts of the electronic device.

Other purposes and advantages of this invention will become apparent from a study of the following portion of this specification, the claims and the attached drawings wherein:

BRIEF DESCRIPTION OF THE DRAWINGS

FIG. 1 is an isometric view of a first preferred embodiment of a thermal fatigue testing apparatus of this invention and employing the method of this invention.

FIG. 2 is an enlarged isometric view of one of the fatigue life test strips shown in FIG. 1.

DESCRIPTION OF THE PREFERRED EMBODIMENT

Figure 3:
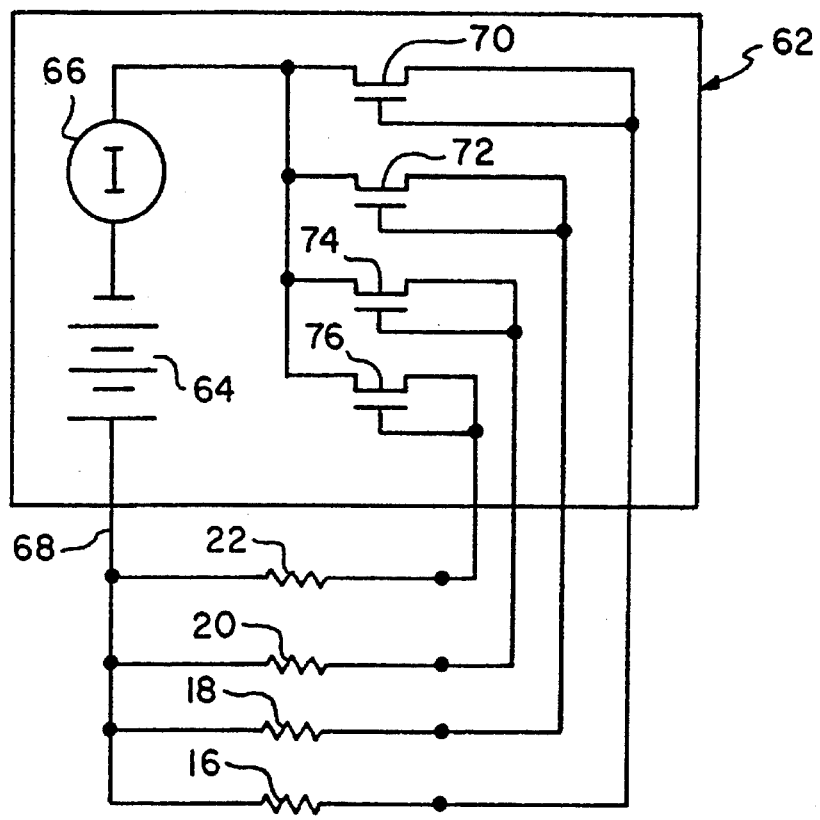
FIG. 3 is an electronic schematic diagram of one way of testing the continuity of the fatigue life test strip shown in FIGS. 1 and 2.

The first preferred embodiment of the thermal fatigue testing apparatus of this invention is generally indicated at 10 in FIG. 1. The apparatus comprises a base 12 which is usually mounted on a substrate 14. The base 12 has a plurality of pockets therein, and closely fitting into each of the pockets is a test strip. Test strips 16, 18, 20 and 22 are illustrated in FIG. 1, and test strip 16 is shown in more detail in FIG. 2. The test strips are made of a different material than the base 12. The anchor ends of the test strips are locked into corresponding pockets in the base and, thus, upon temperature cycling, differential expansion and contraction of the different materials in the test strip and base cause stresses in the test strip. In a particular example, the substrate 14 is a printed wiring board, with conductive paths thereon. When the substrate is organic, such as fiberglass-filled epoxy or other thermosetting resin material, the printed wiring is usually in the form of a copper layer which has been etched into the desired electrical configuration. When the substrate 14 is ceramic, usually the printed wiring thereon is gold deposited thereon. The base 12 may be a semiconductor having an integrated circuit or other electronic devices formed therein. The semiconductor devices may be formed around the pockets which contain the test strips or on the opposite side of the semiconductor base. Sometimes the semiconductor would be incorporated into a package which is then secured to the substrate 14.

In the preferred embodiment, the base 12 is a semiconductor with integrated circuitry formed thereon. Also formed in the base 12, as seen in FIG. 1, is a plurality of pockets, each containing one of the test strips. Pocket 24 is shown in dashed lines for receiving the test strip 16. By defining the test strip, the pocket is also defined. The pocket for the insertion of the test strip is formed by etching.

Referring to FIG. 2, test strip 16 has anchors 26 and 28 formed integrally therewith. The anchors have inner and outer bearing surfaces. Inner bearing surface 30 and outer bearing surface 32 are shown for anchor 26, while inner bearing surface 34 and outer bearing surface 36 are shown for anchor 28. These bearing surfaces are generally flat, with the planes of each bearing surface lying parallel to each other. It is these bearing surfaces which transfer the stresses from the base 12 to the test strip 16. Bridge 38 is of substantially uniform thickness from its top surface 40 to its bottom surface 42 throughout its length. The width of the bridge between left and right sides 44 and 46 varies, being widest close to the anchor and narrowest at the center neck 48. The neck is narrow to provide the stress raiser. The neck is also provided with a stress-raising hole 50. The center neck and stress-raising hole assure that the point of highest stress on the bridge will be at the center so as to define the location which is going to break. In order to concentrate the stresses on the bridge itself at the neck thereof, the base 12 is etched away around the neck. In FIG. 1, the etched-out opening around the neck 48 is indicated at 49. As is seen in FIG. 1, the necks of the bridges 16, 18, 20 and 22 are progressively narrower. Each may have a stress-raising hole at the center of the neck. Each of the other test strips has the same anchors and has the same thickness of bridge, with only the width of the center neck of the bridge varying.

The base 12 is made of a material of lower electrical conductivity, such as a semiconductor or a dielectric. The test strips are each made of the same metal. The base and the test strip materials are chosen to represent the materials associated with the base, substrate, pads on the substrate or connections which are to be tested for thermally caused fatigue. The pockets are made, and the test strips are placed by electroplating them or ion-beam depositing them therein. When the fatigue testing is for connection, adhesion or attachment in the semiconductor environment, the pockets may be quite small, for example, 50 microns long between surfaces 32 and 36. It can be appreciated that the test strips are very small and their pockets are etched into the base. Thus, the regularity of the shapes of the anchors, as shown in FIG. 2, is ideal. Such regularity will not be achieved in practice in such small sizes.

As the structure goes through thermal cycling, the differential coefficient of thermal expansion between the materials of the base and the test strips causes tension and compression of the test strip. Since the center necks of the test strip differ, the stresses thereon are greater with those test strips with the narrower neck. Thus, the test strip with the narrowest neck is expected to separate first.

The thermal coefficient of expansion of the materials of interest; for example, aluminum on silicon or gallium arsenide semiconductor bases, is quite different. The coefficient for aluminum is much higher than for the base material. For example, the thermal coefficient of expansion of aluminum is $11 \times 10^{-6}$ in.xin.$^{-1}\times°$F.$^{-1}$ while the semiconductor materials are in the range of $2 \times 10^{-6}$. What this means is that, if the bridge is deposited at room temperature and thermal cycling raises the temperature, then the bridge goes into compression as the temperature is raised and comes back to 0 tension at room temperature. Even if this type of cycling created the desirable fatigue stresses, since the system returns to 0 tension at room temperature, a break in the bridge might not be electrically detectable since the parts would be lying together. Both from a fatigue viewpoint and from a detection viewpoint, it is desirable to have tension in the test strip at room temperature or normal operating temperature. To accomplish this, the test strip is deposited at an elevated temperature, preferably at about the upper limit of normal operating temperature of the semiconductor device. A temperature of 80° C. is a desirable. In this case, at 80° C., the bridge has 0 tension therein and, as the device cools down to room temperature, the bridge has tension therein. Deposition should not be at too high a temperature in order to avoid stresses in the bridge which approach yield strength.

A sensor circuit 62 is connected to each of the test strips to electrically determine if disconnection occurs. An attachment pad is provided at each end of each test strip. For example, attachment pad 63 is provided at the left end of test strip 16, as seen in FIGS. 1 and 2. Each of the test strips has an attachment pad at each end, as seen in FIG. 1. The test circuit 62 has voltage source 64 and current meter 66 connected in series to line 68, which is connected to one end of all of the test strips. The other end of each of the test strips is connected through its own MOS diode and back to the current meter 66. Test strip 16 is connected through MOS diode 70, and test strip 18 is connected through MOS diode 72. In addition, test strip 20 is connected through MOS diode 74, and test strip 22 is connected through MOS diode 76, all being connected together to the current meter 66. In this circuitry, when there is a failure in a test strip, the corresponding MOS diode permanently opens the circuit. This is for situations in which the test strip may separate under tension, but reclose after the stress is removed. In order to avoid false signals of this nature, the test circuit 62 is provided. In addition, despite the differing resistances in the differing test strips, the MOS diodes will represent substantially equal stepwise increases in resistance as the test strips fail due to the electronic characteristics of the diodes.

The test strips 16–22 are mounted on a base 12 which is preferably a semiconductor base, and the test strips are plated into the pockets on the semiconductor. The semiconductor base 12 is mounted near critical electronic components. On the other hand, the base 12 is the semiconductor chip on which the critical electronic components are formed. While the test strips are shown as lying parallel to each other, such is not a necessary limitation in the layout of test strips on the base 12. They may be laid out in any desirable organization for convenience of space saving, connections, photolithography methods, and deposition procedures. Any convenient physical arrangement on the base is acceptable as long as the several strips are subjected to the proper stresses to achieve the desired fatigue life testing. Because of the small size and proximity of the test strips to the critical electronic components, they will experience the same thermal profile as the host critical electronic components. Since the test strips and base are made of the same materials as the critical electronic components, it will replicate the actual hardware. In thermal cycling causes the same stresses in the test strips as in the critical electronic components. As a result, the test strips measure aging in the host electronic components.

Figure 4:
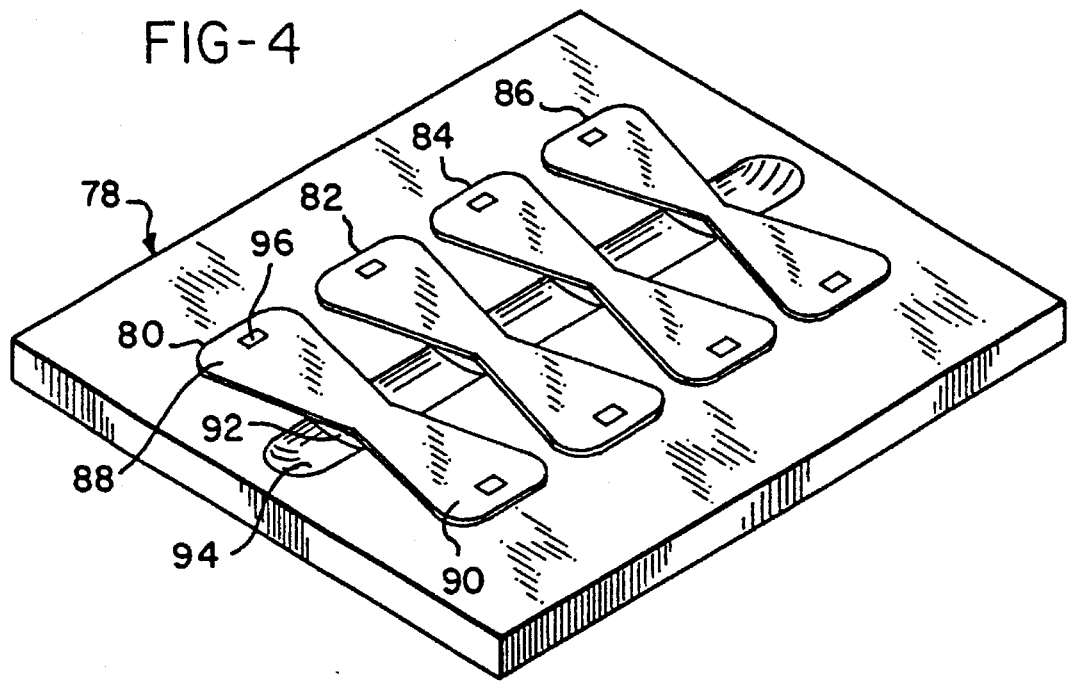
FIG. 4 is an isometric view of a second preferred embodiment of a thermal fatigue testing apparatus in accordance with this invention and employing the method of this invention.

The embodiment of FIG. 4 is an apparatus which represents a second preferred embodiment of the thermal fatigue testing apparatus of this invention. The apparatus of FIG. 4 includes a base 78 on which test strips are mounted. In the present instance, test strips 80, 82, 84 and 86 are illustrated. While four are shown, a larger or lesser number may be employed, depending upon test requirements. The apparatus of FIG. 4 is the same as the apparatus of FIG. 1 except that the test strips are plated onto the top surface of base 78, rather than plated into pockets therein. For the ends of the test strips to be anchored to the base in order to permit the test strips to be stressed and tensioned, the ends of the test strips are large. For example, test strip 80 has a larger triangle 88 on one end and a large triangle 90 on the other separated by neck 92. The triangles on each of the test strips are substantially the same, but they converge to the neck. Each neck is of different width, with the neck 92 wider than the neck on test strip 86. The necks are progressively narrower. The test strips are plated onto the top surface of base 78 in conventional way, such as by plating through a mask opening. In this way, the test strips can be very small, in the order of 50 microns long. The necks can be narrow with the narrowest neck down to the lower limit of manufacturing capability, about 3 microns, and increasing up to about 20 microns.

If the test strips are attached to the base over their entire length, then there would not be localized stress at the neck to provide fatigue life information. In order to free the center part of the test strip under the neck, groove 94 is etched under the neck. As shown in FIG. 4, the groove 94 extends under the necks of each of the test strips. The width of the groove is critical because it is over the width of the groove that the difference in the thermal coefficient of expansion of the two materials is effective.

Each of the test strips is connected to test circuitry, such as that shown in FIG. 3. Two electrical connection pads are provided on each test strip so that the individual continuity of each test strip can be tested and signaled, such as by the circuit of FIG. 3. A connection pad 96 is shown at the left end of test strip 80 in FIG. 4, and a corresponding connection pad is shown at each end of each of the test strips. As with the apparatus 10, the apparatus shown in FIG. 4 has a base of semiconductor material which may be part of or is attached to an integrated circuit chip. The material of the test strips corresponds to another material in the electronic system. It may be a printed wiring conductor material such as copper, nickel, silver or gold, or it may be an attachment material such as solder. Pads are provided on each of the test strips in FIG. 4 so that they may be connected as indicated in FIG. 3. As described above, the plating on of the test strip onto base 78 is preferably accomplished at a raised temperature so that the test strip remains in tension through its operating cycle, which has as its upper limit the normal operating temperature of the semiconductor with which it is associated down to room temperature, which is presumed to be the non-operative temperature of the semiconductor device. In cases where the semiconductor operates over a different temperature range, the temperature of application of the test strip is chosen so that the test strip remains in tension over a substantial portion of its operative range.

The base 12 is preferably part of the semiconductor device itself with the pockets etched into a portion of a semiconductor wafer adjacent electronic components thereon. Alternatively, the base may be the base 78 in the structure of FIG. 4. The base is preferably part of the semiconductor device itself. While such is preferred, the base can be a separate chip attached in another location which experiences the same thermal profile as the host electronic counterpart. The base and test strips are made of the same materials as the hardware in question to replicate the actual hardware experience. In this way, in operation it will measure aging of the host electronic components. The thermal cycling fatigue life is directly monitored by the test circuitry and can provide an always available output signal so that continual fatigue analysis can be achieved. This can be accomplished because the apparatus operates completely passively, except for the resistance measurements made as often as data is desired.

The test strips are stated as being able to be made as small as 50 microns long. The width of the neck of the test strip can be as small as 0.3 micron. The thickness of all of the test strips is preferably equal to aid in the etching process. The size of the anchors is such as to accurately transfer load between the base and the test strips.

This invention having been described in its most preferred embodiment, it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A fatigue testing apparatus comprising:

a substrate;

a base mounted on said substrate, said base including a plurality of pockets, each of said pockets having two anchor recesses etched therein;

a test strip in each of said pockets, each test strip having two anchors and a bridge connecting said anchors, said anchors formed integrally with said bridge, said anchors having inner and outer bearing surfaces to transfer stresses from said base to said test strips, said anchors being configured to be received in said anchor recesses such that changes in dimension between said anchor pockets cause stresses on each of said bridges, wherein each of said test strips are isolated from said base, and wherein said bridges are of different dimensions so that said bridges fail at different fatigue levels; and, means for measuring the electrical resistance of each of said bridges, so that when a bridge fails on one of said test strips from fatigue failure, the failure is electrically indicated.

2. The apparatus of claim 1 wherein said base is a semiconductor and each said bridge is metal.

3. The apparatus of claim 1 wherein each said anchor on each said test strip is substantially the same size and each thickness of said bridge on each of said test strips is of substantially the same thickness, widths of said bridges of each of said test strips being different.

4. The apparatus of claim 3 wherein each said recess is etched into said base.

5. A method of fatigue testing comprising the steps of:

providing a base;

forming a plurality of pockets onto said base by photolithically marking a plurality of pocket outlines onto said base, etching each pocket based upon said outlines, and etching two anchor recesses in each pocket;

forming a plurality of metal test strips within each pocket by depositing, at a temperature elevated above the normal operating temperature of the base, each test strip into said pockets and anchor recesses, each test strip having a bridge with two integral anchors, said anchors having inner and outer bearing surfaces to transfer stresses from said base to said test strips, each bridge having a different size to provide a variety of fatigue failure levels;

repeatedly stressing said bridges with substantially the same force;

electrically testing the continuity of each of said bridges so as to indicate failure from fatigue caused by said stressing;

electrically measuring the resistance of each test strip to indicate fatigue failure thereof; and, signalling said fatigue failure.

6. The method of claim 5 wherein the test strip is deposited on the base by a step selected from the group consisting of electro-deposition, vapor deposition and ion beam deposition.

* * * * *